(12) United States Patent
Petersen

(10) Patent No.: US 7,914,167 B2
(45) Date of Patent: Mar. 29, 2011

(54) SURFACE MODIFYING APPARATUS HAVING ILLUMINATION SYSTEM AND METHOD THEREOF

(75) Inventor: John G. Petersen, Center City, MN (US)

(73) Assignee: 3M Innovative Properties Company, St. Paul, MN (US)

(*) Notice: Subject to any disclaimer, the term of this patent is extended or adjusted under 35 U.S.C. 154(b) by 334 days.

(21) Appl. No.: 12/184,774

(22) Filed: Aug. 1, 2008

(65) Prior Publication Data

US 2010/0027246 A1 Feb. 4, 2010

(51) Int. Cl.
*F21V 33/00* (2006.01)

(52) U.S. Cl. .................. 362/119; 362/253; 362/234

(58) Field of Classification Search .................. 362/119, 362/120, 157, 800, 227, 109, 253, 234; 451/559
See application file for complete search history.

(56) References Cited

U.S. PATENT DOCUMENTS

| | | | |
|---|---|---|---|
| 2,242,229 A | 5/1941 | Burleigh | |
| 2,682,604 A * | 6/1954 | Gerber | 362/91 |
| 3,977,127 A | 8/1976 | Mahnken | |
| 4,782,632 A | 11/1988 | Matechuk | |
| 4,791,700 A | 12/1988 | Bigley et al. | |
| 5,239,783 A | 8/1993 | Matechuk | |
| 5,481,779 A | 1/1996 | Flynn et al. | |
| 5,709,826 A | 1/1998 | Greenberg | |
| 5,957,761 A | 9/1999 | Miller et al. | |
| 6,088,093 A | 7/2000 | Greenberg | |
| 6,132,301 A | 10/2000 | Kaiser | |
| 6,454,428 B1 * | 9/2002 | Bruzon | 362/119 |
| 6,616,295 B2 * | 9/2003 | Sako et al. | 362/119 |
| 2008/0311833 A1 * | 12/2008 | King | 451/356 |
| 2009/0059569 A1 * | 3/2009 | Quattrini, Jr. | 362/119 |

FOREIGN PATENT DOCUMENTS

| | | |
|---|---|---|
| EP | 1287948 A2 | 3/2003 |
| JP | 59107850 A | 6/1984 |
| JP | 61-068855 U | 5/1986 |
| JP | 3017864 U9 | 8/1995 |
| JP | 2008-023694 | 2/2008 |

* cited by examiner

*Primary Examiner* — Bao Q Truong
(74) *Attorney, Agent, or Firm* — Kenneth B. Wood

(57) ABSTRACT

Disclosed are surface modifying apparatus, such as non-motorized and motorized sanding tools, with an illumination system providing an intensity and incidence angle on the working surface that facilitates visual inspection of defects and blemishes on the surface being modified in a safe, low cost, and convenient manner.

20 Claims, 5 Drawing Sheets

SURFACE MODIFYING APPARATUS HAVING ILLUMINATION SYSTEM AND METHOD THEREOF

BACKGROUND

The present description is directed to providing a surface modifying apparatus and method for modifying surfaces. More particularly, the present description is directed to providing a surface modifying apparatus, such as a hand powered sander, with an illumination system for facilitating generally contemporaneous visual inspection and removal of defects in a surface being modified as well as method thereof.

Surface modifying devices, such as hand held powered and non-powered tools have been used for working or modifying a wide variety of surfaces. For example, when fabricating a structure, such as a wall or ceiling it is sometimes necessary to utilize a sanding device to smooth the surface of the structure. For example, interior walls of office building and houses typically use drywall panels. The drywall panels may be attached to wood or metal frames to form interior walls and ceilings. Joints or seams are created along areas where the different dry wall panels are juxtaposed to each other. Typically, the seams are covered with a compound and smoothed. This is to give the appearance that the seams do not exist and provide a wall that is otherwise smooth and flat.

Treating compounds are applied wet to the drywall to fill in the seams and any gaps between the drywall panels. Once dry, the compounds are typically sanded smooth. One kind of hand powered sanding tool generally comprises a sanding sheet wrapped and secured to a sanding block. Another known type of hand held tool assembly for sanding includes a pole sanding tool that comprises a generally rectangular sanding attachment head attached to a handle or pole through a pivoting structure. Pole sander attachment heads have a fixed size and a sponge for supporting sanding paper. An elongate sheet of sanding paper for treating the surface is attached to the fixed sized attachment head. In use, a worker typically pulls the pole for driving the attachment head carrying the sanding paper. As such, the angle between the pole axis and the fixed head attachment varies as the elevation of the attachment head relative to the worker varies. Still other surface modifying apparatus, such as rotary sanders, do not have an effective way to allow users to observe defects around the area being worked and appropriately treat them in an expeditious and time manner.

Sanding steps typically are repeated several times with different sanding grades until seams and gaps appear unnoticeable. The requirements for a smooth and flat finish are quite demanding. Even minor blemishes or defects are usually found to be unacceptable and must, therefore, be removed. Inspection for such blemishes or defects generally follows a worker using a separate source of light, for example a 500 watt halogen light to inspect the working surface after ceasing a sanding operation. Such strong illumination is desired since they are able to have the blemishes and defects cast shadows that are more easily visually discernable. Thereafter, the blemishes or defects are noted and marked and the worker resumes sanding at the marked blemish sites. As such, separation of the sanding and inspection utilizing separate tools tends to add to user operating costs, fatigue of the worker, increased time and higher labor costs.

Accordingly, the foregoing sanding and inspection processes are relatively costly, labor intensive, and time consuming. As a consequence, there is an interest in making the sanding and inspecting operations more efficient from a labor and time standpoint, less costly, and less fatiguing in practice.

SUMMARY

The present description is directed to a surface modifying apparatus. The apparatus comprises: a housing assembly including a major surface attachable to a surface modifying article; and a source of illumination coupled to the housing assembly and operable for projecting a beam of light to an area to be illuminated on a working surface adjacent at least a portion of a periphery of the housing assembly with sufficient intensity and at a generally consistent and shallow angle, thereby creating shadows, by defects located at and below the surface to be modified, that are visually discernable.

The present description is directed to a method of modifying a working surface. The method comprises: providing a surface modifying article attached to a major surface of a housing assembly; projecting at least a beam of light from a source of illumination coupled to the housing assembly and operable for projecting a beam of light to an area to be illuminated on a working surface adjacent at least a portion of a periphery of the housing assembly with sufficient intensity and at a generally consistent and shallow angle, thereby creating shadows, by defects located at and below the surface to be modified, that are visually discernable.

The present description is directed to an accessory adapted to be used, in combination, with a surface modifying apparatus having a housing assembly. The accessory comprises: an accessory housing assembly, and a source of illumination coupled to the housing assembly and operable for projecting a beam of light to an area to be illuminated on a working surface adjacent at least a portion of a periphery of the housing assembly with sufficient intensity and at a generally consistent and shallow angle, thereby creating shadows, by defects located at and below the surface to be modified, that are visually discernable.

The present description is directed to a pad assembly comprising: a rotatable member having first and second opposing major surfaces; and a source of illumination coupled to the housing assembly and operable for projecting a beam of light to an area to be illuminated on a working surface adjacent at least a portion of a periphery of the housing assembly with sufficient intensity and at a generally consistent and shallow angle, thereby creating shadows, by defects located at and below the surface to be modified, that are visually discernable.

One aspect of the present description is for accomplishing surface modification and inspection in a timely manner that improves surface modifying efficiency and ease of work inspection by a worker.

Another aspect of the present description is for accomplishing the above in a manner that provides a source of illumination on a surface modifying hand tool that generates light incident onto a working surface with sufficient illumination and at a shallow and consistent angle to more easily observe defects and blemishes on a working surface.

Another aspect of the present description is for accomplishing the above in a manner that generally contemporaneously allows for inspection of surface blemishes or defects, and prompt surface modification of the working surface.

Another aspect of the present description is for accomplishing the above in a manner that generally contemporaneously allows for inspection of surface blemishes or defects, generally immediately followed by surface modification of the working surface by a hand-held tool without removing the hand tool from a wall.

Another aspect of the present description is for accomplishing the above in a manner that generally contemporaneously allows for inspection of surface blemishes or defects, generally immediately followed by surface modification of the working surface by a motorized hand-held surface modifying tool without removing the hand tool from a wall.

Another aspect of the present description is for accomplishing the above in a manner that generally contemporaneously allows inspection of surface defects or blemishes and their removal by a single, hand-held tool without removing the hand tool from a working surface, such as a wall.

Another aspect of the present description is for accomplishing the above in a manner that provides enhanced safety by providing a lower power source of illumination that does not generate excessive heat thereby being particularly useful in situations involving non-motorized, hand-held surface modifying system.

Another aspect of the present description is for an accessory that may be attached to a surface modifying apparatus and/or a pad assembly and the like.

Another aspect of the present description is for a pad assembly, such as a backup pad assembly attachable to a surface modifying apparatus that has a source of illumination of the kind noted above attached thereto.

Another aspect of the present description is to accomplish the above in a manner that is cost effective to manufacture, assemble and use.

The aspects described herein are merely a few of the several that can be achieved by using the present description. The foregoing aspects do not suggest that the present description must only be utilized in a specific manner to attain the foregoing aspects.

DETAILED DESCRIPTION

The words "a," "an," and "the" are used interchangeably with "at least one" to mean one or more of the elements being described. By using words of orientation, such as "top," "bottom," "overlying," "front," and "back" and the like for the location of various elements in the disclosed articles, I refer to the relative position of an element with respect to a horizontally-disposed body portion.

Figure 1:
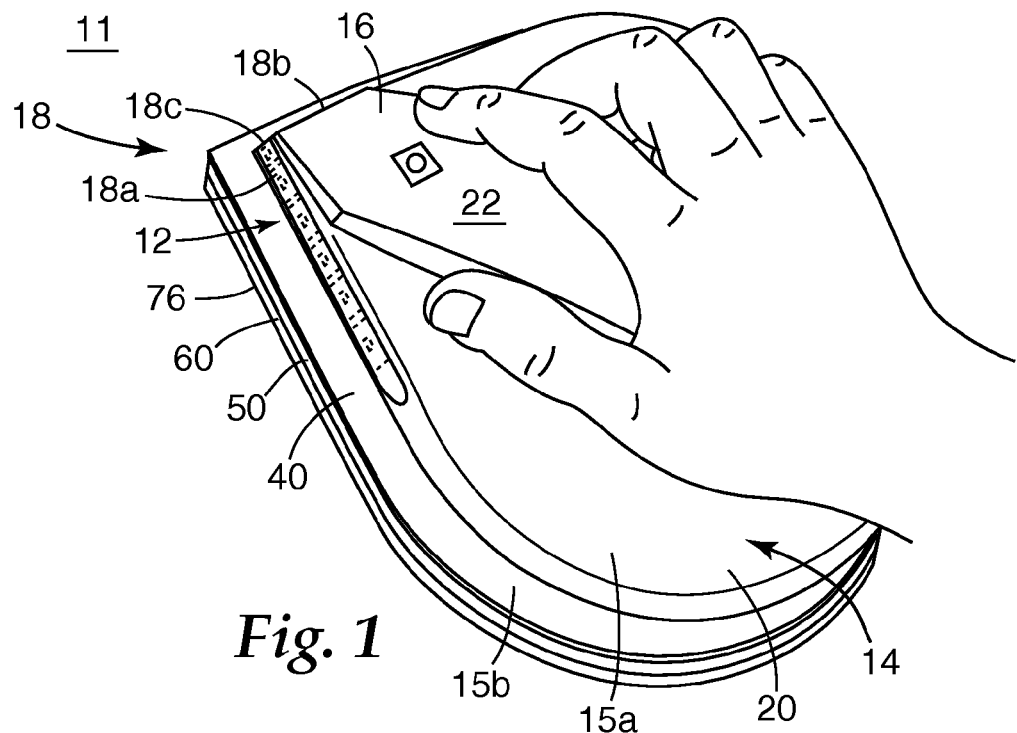
FIG. 1 is perspective view of a user manipulating a hand sanding device of one exemplary embodiment along a working surface of a panel or the like without the illumination system of the present description being energized.

FIG. 1 illustrates one exemplary embodiment of a surface modifying apparatus 10, such as a non-motorized hand sanding device 10 for treating a generally planar working surface 11, such as a wall, ceiling or other similar structure. The hand sanding device 10 includes an illumination system 12 made consistent with the principles of the present description. While a hand sanding device 10 is described, the present description envisions that a variety of hand tools may be used to modify a working surface. Surface modification includes, but is not limited to sanding, polishing, cleaning, painting and the like. While the hand sanding device 10 is described as being non-motorized, it will be appreciated that it may be motorized and/or provided with additional devices, such as a vacuum device and the like.

The hand sanding device 10 includes a member 14 or housing assembly 14 that includes an upper body portion 15a and a lower body portion 15b. The upper body portion 15a may be comprised of a shell-like structure that accommodates the components described herein. In an illustrated exemplary embodiment, the upper body portion 15a may be made of a lightweight suitable thermoplastic material. Other suitable materials may be used and these include, but are not limited to, metals, composite materials, wood, or the like. The upper body portion 15a has a hand gripping portion 16. In the illustrated exemplary embodiment, the upper body portion 15a has a tapered leading edge portion 18 with leading edge portions 18a and 18b converging toward each other and terminating in a leading edge 18c to provide a wedge shape. The upper body portion 15a may have a rounded trailing edge 20. The housing assembly 14 may have a wide variety of sizes and configurations to assist a user in working a working surface. In the exemplary embodiment, the hand gripping portion 16 includes a raised portion 22 in order to enable a user to grasp and guide the hand sanding device 10 along a walled surface in order to inspect the latter and correct defects. Typically, defects of the kind that are to be treated may range in size from about 1-5 mil at and below the surface. It will be appreciated that the present description envisions a wide variety of configurations for the handle or hand gripping portion 16. In the illustrated exemplary embodiment, the hand gripping portion 16 may have a variety of sizes and configurations to facilitate guiding the tool.

Figure 2:
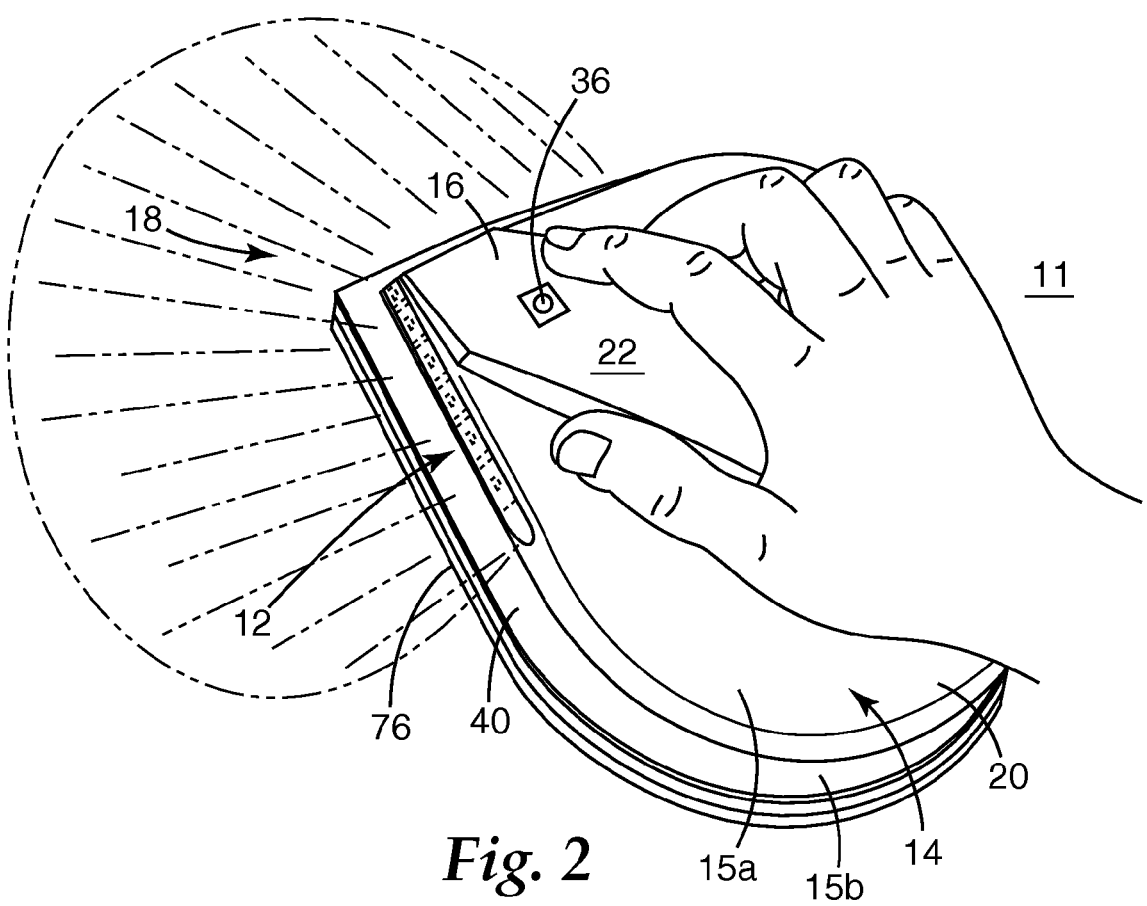
FIG. 2 is a view similar to the hand sanding device depicted in FIG. 1, but with the illumination system activated to generate a field of illumination onto the surface being worked.

The illumination system 12 in the exemplary embodiment is mounted on the upper body portion 15a so as to assume a position wherein it may direct or project light beams toward an area 30 or a field of illumination 30 (FIG. 2) for observing any defects in a finish of such surface. Once the blemishes are located they can then be almost immediately removed without a break in the sanding and the necessity of a separate high powered light source to conduct inspections.

The illumination system 12 may comprise a portable source of power, such as replaceable batteries (not shown). The replaceable batteries may be situated within a compartment (not shown) of the upper body portion 15a. An actuating switch 36 is mounted on the upper body portion 15a and is operatively electrically coupled to a known kind of circuit (not shown) including the power source and the source of illumination 12 for allowing a user to control energization of the latter. A variety of switches are contemplated for turning on and off the illumination system 12. While a known type of battery power is provided, the present description envisions the use of other sources of power, such as solar and the like. In addition, the source of power for the illumination system 12 may be through a power cord (not shown) to an external source of power.

With continued reference to the housing assembly, the lower body portion 15b may include a solid generally planar body member 40 that has first and second major surfaces 42 and 44, respectively. The body member 40 may be made of a generally rigid, low density, and lightweight material. Advantageously, the lightweight material serves to minimize user fatigue during sanding. In addition, a rigid backing for surface modifying articles, such as abrasive pads and the like tend to make for a smoother finish. The rigidity is useful from a standpoint of enabling a user to apply pressure more uniformly to a surface modifying article being carried thereby. The rigid and lightweight material may be made of a molded lightweight, low density, relatively strong, and stiff thermoplastic material. For example, the material may be a molded block of a rigid polyurethane material, or a rigid polystyrene block. Other similar and suitable materials may be used that may include, but are not limited to polyolefin, polyurethane, and combinations thereof. The first major surface 42 is attached as by any suitable approach to a bottom surface of the upper body portion 15a while the major surface 44 is attached to an attaching layer 50.

The attaching layer 50 may be provided for securing a surface modifying article 60 to the housing assembly 14. The attaching layer 50 may be any known attaching system for securing permanently or releasably the surface modifying article 60 to the housing assembly 14. The attaching pad 50 or layer 50 may include, but not be limited to having, a releasable mechanical type attachment mechanisms on a major opposing surface, such as hook and loop fasteners, pressure sensitive adhesives, and the like. In the exemplary embodiment, the attaching layer 50 may have a pressure sensitive adhesive coating 52 on an upper major surface thereof to be releasably connected or attached to the major surface 44 of the lower body member 40, and hook elements of a hook and loop fastening arrangement (not shown) on a major surface 54 that is adapted to be releasably secured to the surface modifying article 60. Other known kinds of suitable releasable mechanical type attachment mechanisms may be used including, but not limited to, pressure sensitive adhesives.

The surface modifying article 60 may include a foam backed pad 62 or layer 62 that has a releasable connection with the hook elements of the attaching layer 50. The other major surface of the surface modifying article 60 may have coated thereon a suitable surface modifying abrasive layer 64. While an abrasive layer 64 to sand dry wall is described herein, other surface modifying surfaces may be provided as noted above. It will be appreciated that a wide variety of matable releaseable mechanisms may be used for securing the surface modifying article 60 to the attaching pad 50. While the foregoing construction is used, it will be appreciated that a wide variety of surface modifying articles and methods of attachment may be used.

Figure 3:
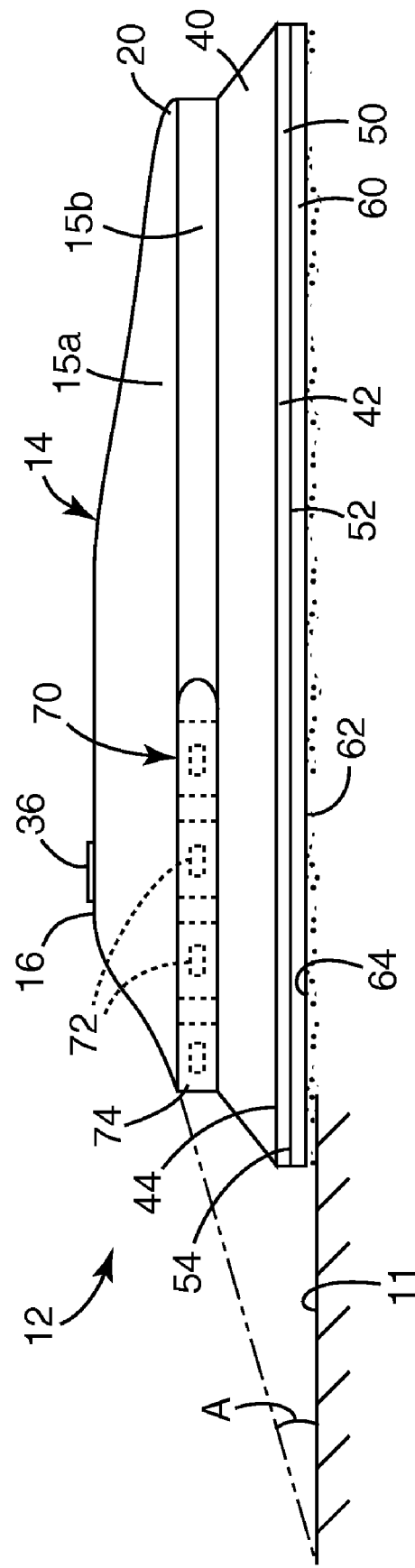
FIG. 3 is an elevation view of the hand sanding device of the present description as illustrated in FIGS. 1 and 2.

Reference is now made to the illumination system 12 which may include one or more arrays 70 of a plurality of sources of illumination 72. The illumination system 12 directs or projects beams of light of relatively high intensity and at shallow angles relative to the surface to be worked. The sources of illumination may include light-emitting diodes 72 having a protective transparent lens cover 74 that projects beams at an angle of incidence A (FIG. 3) to the surface to be treated so as to create shadows of the defects or blemishes to facilitate their removal. Each array may include any appropriate number of light-emitting diodes. In the present embodiment, there may be five light-emitting diodes. It will be further appreciated that each of the light-emitting diodes may be provided with a reflector. It will be understood that the combination of the shallow angles of the beams and the intensity of the beams are sufficient to generate visually discernable shadows indicative of the very small defects or blemishes that are intended to be removed.

The light-emitting diodes 72 are at a fixed height relative to the surface to be treated. Also, it has been determined that the closer the light-emitting diodes 72 are to the plane of the working surface the better the results are in terms of generating shadows and thereby observing defects or blemishes on such surfaces. For a hand-held tool of the present exemplary embodiment, the light-emitting diodes 72 may each provide between about 10-100 lumens, 0.25 to 5.00 watts, and use between 1.50 to about 5.00 volts. A nominal 3.60 volts at 350 ma may be used. The light-emitting diode may provide 10 to about 50 lux @ 1 meter using a flat lens or wide angle lens. In one example, an angle of incidence A at about 14 degrees is provided such that the illumination area 30 has an effective range of about 3 inches from the periphery.

While the light-emitting diodes 72 are used, the present description envisions using other artificial light sources, such as incandescent and fluorescent light sources. Advantageously, the light-emitting diodes, in general, do not generate significant amounts of heat or require significant amounts of power. In addition, the light-emitting diodes are more durable. These factors are advantageous from a cost standpoint and the standpoint of allowing a user to safely handle the sanding mechanism for prolonged periods without any harmful heat affects.

As noted, the angles of incidence of the beams should be relatively shallow. It has been determined that such shallow angles may be in the order of about 45 degrees or less to make shadows that are readily discernable to visual inspection. Angles outside of 45 degrees generally do not generate shadows that are readily visible. Accordingly, the effective range of the light beams may not exceed the height of the light source from the working surface. Ideally, the angles of incidence may vary to be less than about 20 degrees or even about 15 degrees or less. Accordingly, the lens 74 and/or the angular positioning of the light-emitting diodes 72 may combine to define the angle of incidence that will enhance renderings of the shadows. Therefore, the light-emitting diodes 72 provide an angle of incidence "A" relative to the working surface that remains consistent regardless of the position of the sanding device relative to the user. This is an improvement over known systems that employ lights on handles and the like.

In the illustrated exemplary embodiment, a pair of linear arrays 70 converge of the sources of light converge toward the leading edge 18c. In one exemplary embodiment, the light-emitting diodes 72 may be of a type that generates visible light in response to actuation thereof by the switch 36. Other spectral frequencies may be used to illuminate the working surface depending on the kind of defects to be observed. The intensity of the light emitted is sufficient to enable a user to discern defects and damage in the working surface while being able to continue working, thereby expeditiously shortening the time to complete a particular job. In this regard, the output of the beams individually and collectively will provide sufficient intensity to illuminate an area 30 or field of illumination 30 that extends from the periphery 76 of the hand sanding device 10 by a sufficient amount to allow the user to observe the defects and continue sanding at the same time.

While the exemplary embodiment depicts beams being generated from adjacent at least a portion of the periphery 76, it will be understood that the light-emitting diodes 72 may extend or wrap around the entire periphery. It will be also understood that the light-emitting diodes 72 and/or the transparent lens cover 74 may be constructed to modify distribution or composition of the beams.

Advantageously, there is no significant separation in terms of time between observing defects and correcting for them by sanding. In addition, there is no requirement for a separate lighting device to be used.

Figure 4:
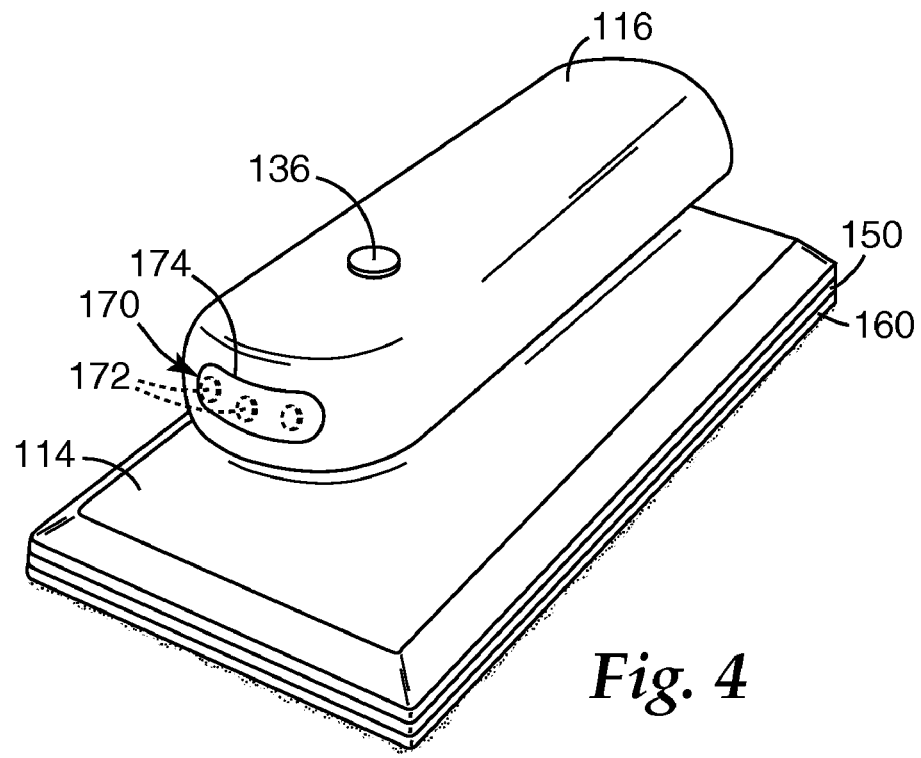
FIG. 4 is a perspective view of a hand sanding device of another exemplary embodiment of the present description without the illumination system of the present description being energized.
Figure 5:
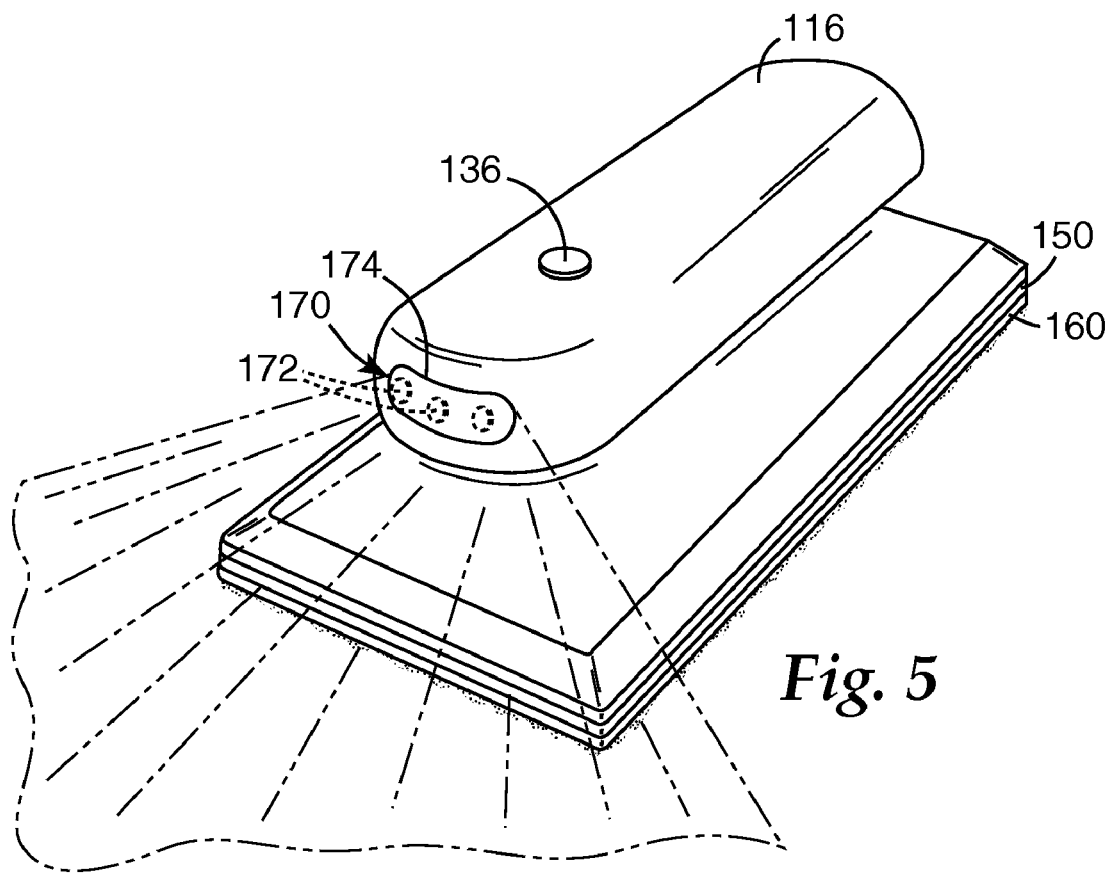
FIG. 5 is a view similar to the hand sanding device depicted in FIG. 4, but with the illumination system activated to generate a field of illumination onto a surface being worked.

Reference is now made to the exemplary embodiment of FIGS. 4-5 which illustrate another exemplary embodiment of the present description. This embodiment is somewhat similar to the previous embodiment and similar structure will be identified the same reference numeral with the addition of a prefix "1". The light-emitting diodes 172 extend a collective beam or area of illumination from a leading portion of an elongated hand gripping portion 116 or handle 116 toward the working surface 11 immediately ahead of the direction of movement for the sanding device at an angle of incidence of about no greater than 45 degrees and preferably, no greater than 30 degrees. Ideally, the range of about 15-20 degrees may be used. In this exemplary embodiment, while the light-emitting diodes 172 are on front portion of the handle 116 they may be positioned at other locations on the sanding device 110. In addition, there are fewer individual light-emitting diodes used in this array, so the intensity of the light emitting diodes may be increased accordingly as is consistent with the teachings of the present description. A switch 136 for actuating the array of light-emitting diodes is conveniently located on the handle to turn on and off the power from a portable battery (not shown). Also, the housing assembly 114 may have attached thereto an attaching pad 150 as well as a surface modifying article 160.

Figure 6:
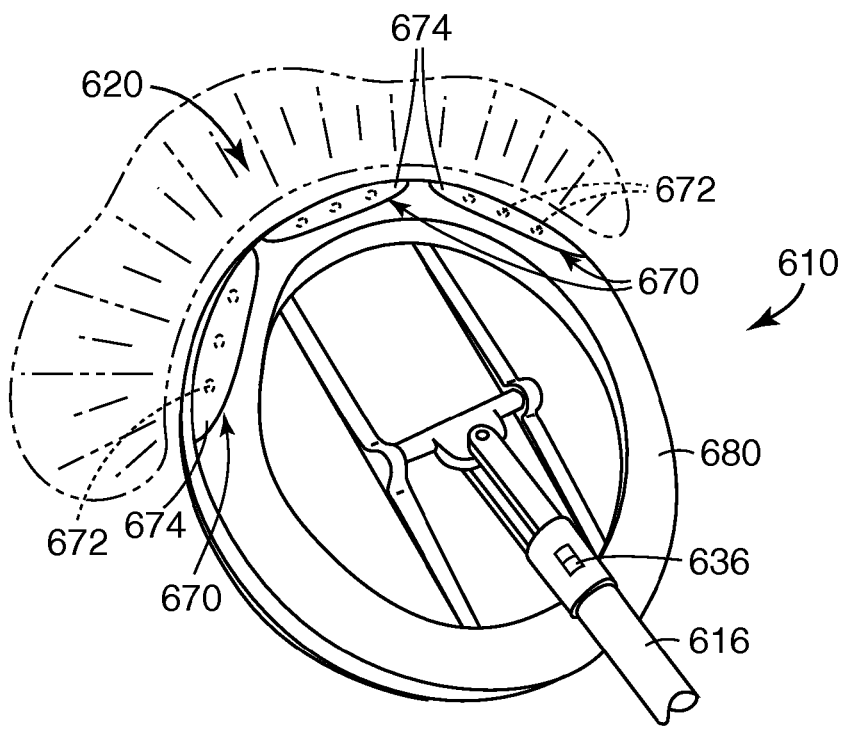
FIG. 6 is a perspective view of a non-motorized pole sanding device illustrating another exemplary embodiment of the illumination system of the present description.

Reference is now made to the embodiment of FIG. 6 which illustrates another exemplary embodiment of the present description. FIG. 6 illustrates a known type of surface modifying mechanism 610, such as a pole sander 610 having a source of illumination 620. In this regard, the source of illumination 620 includes a plurality of arrays 670 of light-emitting diodes 672 of the kind identified above behind lenses 674. The arrays 670 may be positioned circumferentially around at least a portion of or the entire periphery of the pole sander 610 in a stationary circular housing assembly 680. The housing assembly 680 may act as an accessory that is mounted by any suitable mechanism (not shown) to a stationary part of the pole sander. Alternatively, the housing assembly 680 may form an integral part of the pole sander 610 so as to be a one-piece unit. The stationary housing assembly 680 may house not only the light-emitting diodes 672, but a portable source of power (not shown). The housing assembly 680 may be attached to the periphery of the pole sander 610. A switch 636 on a handle 616 on the surface modifying mechanism 610 is operatively electrically connected to the source of illumination 620 and a source of power for turning on and off the power to the source of illumination. The power may also be provided by an external source that is used for the pole sander 610. Advantageously, as noted, by having the source of illumination positioned, as in the present embodiment, there is provided a consistent angle and shallow angle of light incident on the surface to be treated. This is so regardless of the angle the pole of the pole sander assumes during surface treating. It will be appreciated that if the light source were on the pole, the shallow angle would not be consistent, but would vary as the pole is pulled across the surface. Accordingly, the beam may not be at a shallow angle to the working surface.

Figure 7:
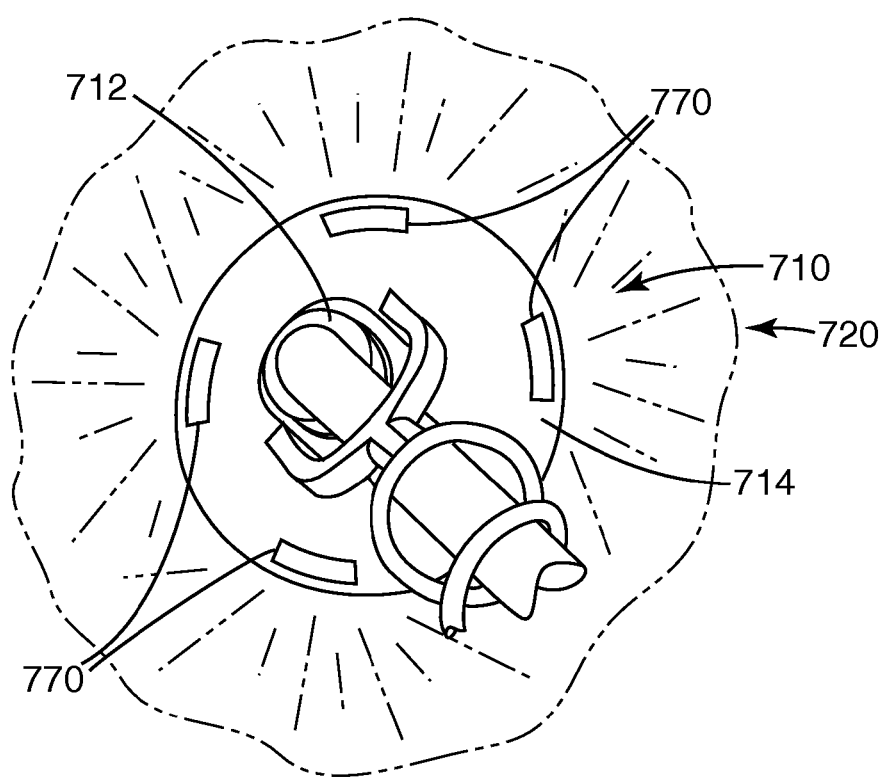
FIG. 7 is a perspective view of a motorized sanding device illustrating another exemplary embodiment of the illumination system of the present description.
Figure 8:
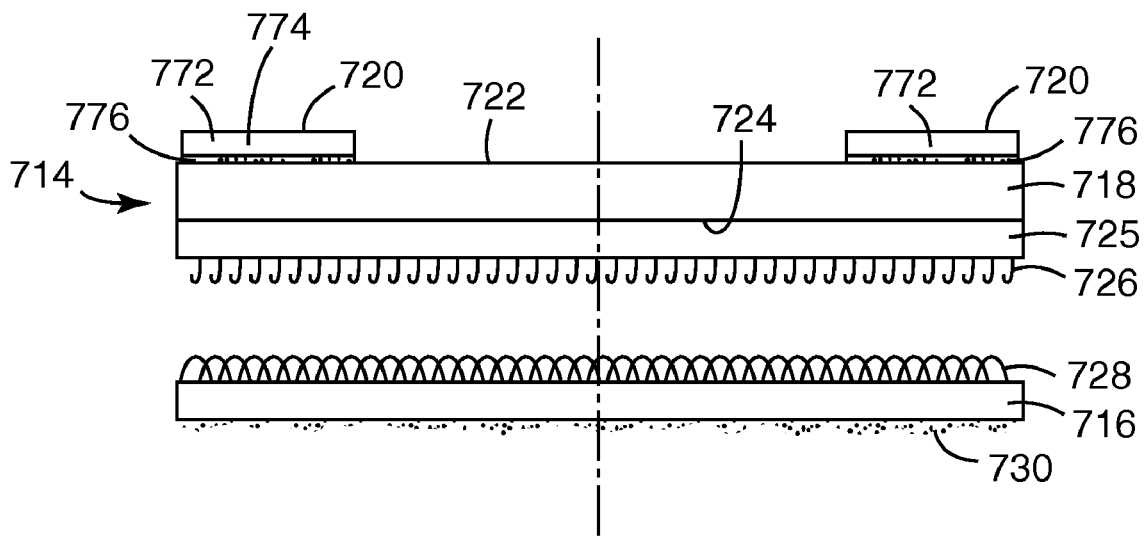
FIG. 8 is a schematic of a back-up pad assembly of the present description.

Reference is now made to the embodiment of FIGS. 7 & 8 which illustrate another exemplary embodiment of the present description. FIG. 7 illustrates a known type of surface modifying mechanism 710, such as an orbital sander 710 having in combination therewith a source of illumination 720. In this exemplary embodiment, the orbital sander 710 has a stationary housing portion 712 located at the hub of the sander that includes a rotary motor (not shown) for driving a rotor (not shown) that is attached to a back-up pad assembly 714 in a known manner. The rotary sander is operated in a known manner and may be one that is commercially available from 3M Corporation, St. Paul, Minn. While the present embodiment is in the context of a rotary sander, it will be understood other surface modifying apparatus that move a surface modifying articles may be used. In normal usage, the back-up pad assembly 714 is rotated to drive a surface modifying article 716 (FIG. 8) attached to the back-up pad assembly over the surface to be treated so as to create a generally circular field of illumination resulting from the light-emitting diodes mounted to a rotating portion of the motorized tool.

FIG. 8 illustrates one exemplary embodiment of a back-up pad assembly 714. The back-up pad assembly 714 may include a generally circular-shaped and planar base member 718 made of a backing material that has opposed first and second major surfaces 722 and 724, respectively. As is known, the back-up pad assembly 714 may be connected to the rotor by a fastener (not shown) or other similar device(s) joining the center of the back-up pad assembly to the rotor. The second surface 724 may include releaseable mechanical attaching members, such as hooks 726 for releaseable securing to loop type attaching members 728 on the surface modifying article 716. The surface modifying article 716 may include an abrasive surface 730 on one major surface thereof for modifying the surface to be treated. Such a surface modifying article may be one that is commercially available from 3M Corporation, St. Paul, Minn. as a HookIt™ and HookIt™ II sanding member. Other similar and suitable surface modifying articles may be used consistent with the teachings of the present description.

According to the present description, the source of illumination 720 including the arrays 772 of light-emitting diodes are mounted as an accessory directly on the first surface 722 adjacent its periphery. The light-emitting diodes are fixedly mounted in a manner, as noted, to provide a consistent and shallow angle of illumination. Alternatively, the arrays 772 of the light-emitting diodes may be mounted on the first surface 722 so as to provide a one-piece construction. In the exemplary embodiment, wherein the arrays 772 act as accessories, they may include a housing 774 having a portable source of power (not shown) therein and an adhesive layer 776 connected to an exterior mounting surface that is to be connected the first surface of the body member. The adhesive layer 776 may be a pressure sensitive adhesive. Other suitable mechanisms for making a connection are contemplated. As so mounted, rotation of the back-up pad assembly 714 with the light-emitting diode arrays 772 connected thereto serves to direct the illumination at a consistent and shallow angle to the surface being modified even while the arrays are being rotated. These areas of interest will be effectively illuminated. This provides great versatility with rotating sanders and the like.

Figure 9:
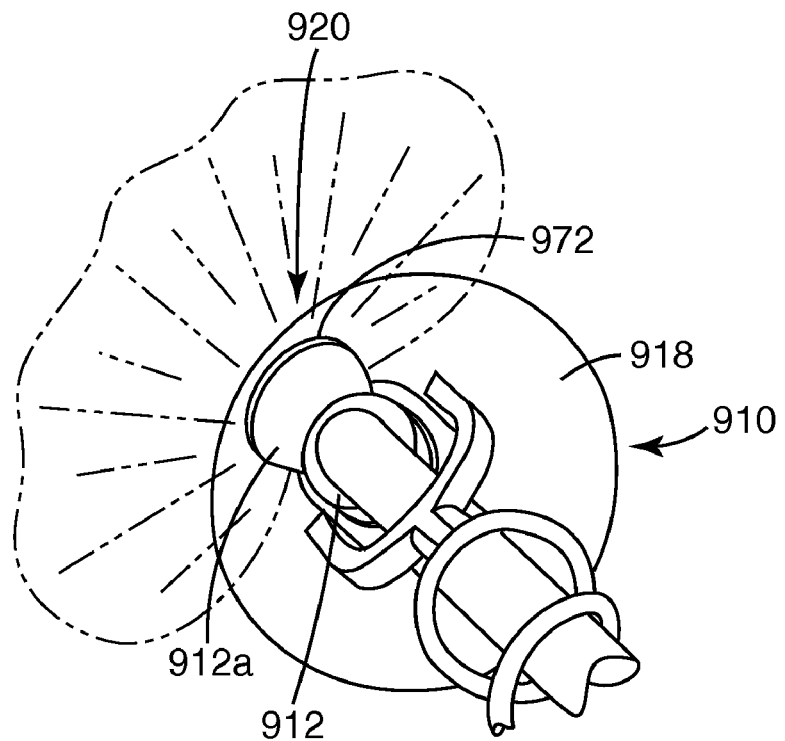
FIG. 9 is a perspective view of another exemplary embodiment which includes a source of illumination arrangement.

FIG. 9 illustrates yet another exemplary embodiment, wherein the surface modifying apparatus 910 may include an orbital sander device 910 that includes a stationary portion 912 or member 912. The stationary portion 912 may include a projecting segment 912a extending close to the periphery of a back-up pad assembly 918 as illustrated. An array 972 of light-emitting diodes (not shown) being internally battery powered may be mounted on the segment 912a so as to illuminate the surface to work in the manner earlier described. The foregoing illustrated embodiment is but one of many different configurations that enable the source of illumination to be mounted so as to obtain the illumination for clearly observing defects by creating shadows of defects.

This present description may take on various modifications and alterations without departing from the spirit and scope. Accordingly, this present description is not limited to the above-described exemplary embodiments, but is to be controlled by limitations set forth in the following claims and any equivalents thereof. This present description also may be suitably practiced in the absence of any element not specifically disclosed herein. All patents and publications noted above, including any in the Background section are incorporated by reference into this document in total.

What is claimed is:

1. A surface sanding apparatus comprising:
a housing assembly including a major surface attachable to a surface sanding abrasive article; and
a source of illumination coupled to the housing assembly and operable for projecting a beam of light to an area to be illuminated on a working surface adjacent at least a portion of a periphery of the housing assembly with sufficient intensity and at a generally consistent and shallow angle thereby creating shadows, by defects located at and below the surface to be sanded, that are visually discernable.

2. The apparatus of claim 1, wherein the source of illumination is in close proximity and at a fixed height relative to the major surface.

3. The apparatus of claim 1, wherein the fixed height does not generally exceed the linear extent of an effective range of the area of illumination from the periphery of the housing assembly.

4. The apparatus of claim 1, wherein the shallow angle is in a range of about 45 degrees or less.

5. The apparatus of claim 4, wherein the range of the shallow angle is about 15 degrees.

6. The apparatus of claim 1, wherein the source of illumination includes a plurality of light-emitting diodes.

7. The apparatus of claim 6, wherein the source of illumination includes a lens that directs the beams of the light-emitting diodes to the area to be illuminated.

8. The apparatus of claim 1, further including a sanding abrasive article attached to the housing assembly.

9. The apparatus of claim 8, wherein the sanding abrasive is attached by an attaching layer to a major surface of a generally planar body member of the apparatus.

10. The apparatus of claim 1, wherein the housing assembly includes an upper body portion adapted to be gripped by a hand for non-motorized movement of a surface sanding article over a working surface, and wherein the major surface of the housing assembly of the apparatus opposes the gripping portion and is a surface of a generally planar body member and is adapted to be coupled to a surface sanding article.

11. The apparatus of claim 10, wherein the housing assembly comprises a wedge shape with first and second leading edge portions that converge toward each other and wherein the source of illumination comprises a pair of linear arrays of illumination sources each of the pair of linear arrays being mounted along a leading edge portion of the housing assembly.

12. The apparatus of claim 1, wherein the housing assembly includes: a rotary portion defining a major surface to be connected to a surface sanding article, a stationary portion, a handle is pivotally connected to the stationary portion for pulling the housing assembly over a working surface, and a source of motive power on the stationary portion for driving the rotary portion; wherein the source of illumination is coupled to the stationary portion to project the beam to the area adjacent the periphery of the rotary portion.

13. The apparatus of claim 1, wherein the source of illumination includes a self-contained portable source of power.

14. The apparatus of claim 1, further comprising a switch actuatable for controlling operation of the source of illumination.

15. The apparatus of claim 14, wherein the housing assembly is made of a generally rigid and lightweight material.

16. The apparatus of claim 1, wherein the housing assembly includes a rotatable member having a first major surface and a second major surface, the second major surface adapted to have attached thereto a surface sanding article.

17. A method of sanding a working surface, the method comprises:
providing a surface sanding article attached to a major surface of a housing assembly;
projecting at least a beam of light from a source of illumination coupled to the housing assembly to an area of illumination on a working surface adjacent at least a portion of a periphery of the housing assembly with sufficient intensity and at a generally consistent and shallow angle thereby creating shadows, by defects located at and below the surface to be sanded, that are visually discernable, and
sanding a working surface with the surface sanding article.

18. The method of claim 17, wherein the beam is projected from a location in close proximity to the major surface and at a fixed height relative to the major surface.

19. The method of claim 17, wherein the fixed height does not generally exceed a linear extent of an effective range of the area of illumination of from the periphery of the housing assembly.

20. The method of claim 17, wherein the shallow angle is in a range of about 45 degrees or less.

* * * * *